United States Patent
Dehghan Marvast et al.

(10) Patent No.: US 10,531,807 B2
(45) Date of Patent: Jan. 14, 2020

(54) AUTOMATED EXTRACTION OF ECHOCARDIOGRAPH MEASUREMENTS FROM MEDICAL IMAGES

(71) Applicant: International Business Machines Corporation, Armonk, NY (US)

(72) Inventors: Ehsan Dehghan Marvast, Palo Alto, CA (US); Allen Lu, New Haven, CT (US); Tanveer F. Syeda-Mahmood, Cupertino, CA (US)

(73) Assignee: International Business Machines Corporation, Amonk, NY (US)

(*) Notice: Subject to any disclaimer, the term of this patent is extended or adjusted under 35 U.S.C. 154(b) by 70 days.

(21) Appl. No.: 15/848,077

(22) Filed: Dec. 20, 2017

(65) Prior Publication Data
US 2019/0183366 A1   Jun. 20, 2019

(51) Int. Cl.
*G16H 30/40* (2018.01)
*G06K 9/62* (2006.01)
*G06T 7/00* (2017.01)
*A61B 5/00* (2006.01)
*A61B 8/00* (2006.01)
(Continued)

(52) U.S. Cl.
CPC ........ *A61B 5/0402* (2013.01); *A61B 5/04012* (2013.01); *A61B 5/72* (2013.01); *G06K 9/6217* (2013.01); *G06T 7/0012* (2013.01); *G06K 9/20* (2013.01); *G16H 10/60* (2018.01)

(58) Field of Classification Search
CPC ... A61B 5/0402; A61B 8/5223; A61B 8/0883; A61B 5/04012; A61B 5/72; G06T 7/62; G06T 7/0014; G06T 7/0012; G06T 2207/30048; G06T 2207/20084; G06T 2207/20081; G06T 2207/10132;
(Continued)

(56) References Cited

U.S. PATENT DOCUMENTS

| 9,968,257 | B1* | 5/2018 | Burt | A61B 5/7267 |
| 2012/0027276 | A1* | 2/2012 | Chono | A61B 5/02028 382/128 |

FOREIGN PATENT DOCUMENTS

CN    107169526 A    9/2017

OTHER PUBLICATIONS

Dong et al. "A Combined Multi-scale Deep Learning and Random Forests Approach for Direct Left Ventricular Volumes Estimation in 3D Echocardiography." Computing in Cardiology Conference, Sep. 11, 2016, pp. 889-892 (Year: 2016).*

(Continued)

*Primary Examiner* — Jon Chang
(74) *Attorney, Agent, or Firm* — Stephen J. Walder, Jr.; William J. Stock

(57) ABSTRACT

Mechanisms are provided to implement an automated echocardiograph measurement extraction system. The automated echocardiograph measurement extraction system receives medical imaging data comprising one or more medical images and inputs the one or more medical images into a deep learning network. The deep learning network automatically processes the one or more medical images to generate an extracted echocardiograph measurement vector output comprising one or more values for echocardiograph measurements extracted from the one or more medical images. The deep learning network outputs the extracted echocardiograph measurement vector output to a medical image viewer.

18 Claims, 5 Drawing Sheets

(51) Int. Cl.
*A61B 5/0402* (2006.01)
*A61B 5/04* (2006.01)
*G06K 9/20* (2006.01)
*G16H 10/60* (2018.01)

(58) Field of Classification Search
CPC ...... G16H 30/40; G16H 10/60; G06K 9/6217; G06K 9/20
See application file for complete search history.

(56) References Cited

OTHER PUBLICATIONS

Elhoseiny, Mohamed et al., "A Comparative Analysis and Study of Multiview CNN Models for Joint Object Categorization and Pose Estimation", Proceedings of the 33rd International Conference on Machine Learning, Jun. 19-24, 2016, 10 pages.

High, Rob, "The Era of Cognitive Systems: An Inside Look at IBM Watson and How it Works", IBM Corporation, Redbooks, Dec. 12, 2012, 16 pages.

Li, Yifeng et al., "A review on machine learning principles for multi-view biological data integration", Briefings in Bioinformatics, Dec. 22, 2016, pp. 1-16.

Yi, Darvin et al., "Optimizing and Visualizing Deep Learning for Benign/Malignant Classification in Breast Tumors", 29th Conference on Neural Information Processing Systems (NIPS 2016), arXiv: 1705.06362v1, May 17, 2017, 9 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

International Search Report and Written Opinion dated Apr. 24, 2019 for International Application No. PCT/IB2018/059901, 8 pages.

\* cited by examiner

AUTOMATED EXTRACTION OF ECHOCARDIOGRAPH MEASUREMENTS FROM MEDICAL IMAGES

BACKGROUND

The present application relates generally to an improved data processing apparatus and method and more specifically to mechanisms for performing automated extraction of echocardiograph measurements from medical images.

An echocardiogram, also sometimes referred to as a diagnostic cardiac ultrasound, is a well accepted medical test that uses high frequency sound waves (ultrasound) to generate an image of a patient's heart. The echocardiogram uses the sound waves to create images of the heart's chambers, valves, walls, and blood vessels (aorta, arteries, veins) attached to the heart. During an echocardiogram, a probe, referred to as a transducer, is passed over the patient's chest and is used to produce the sound waves that bounce off the structures of the heart and "echo" back to the probe. The detected "echoes" are converted into digital images that may be viewed on a computer display.

Echocardiograms are used to identify a variety of different heart conditions of patients as well as provide medical personnel information about the structure and functioning of the heart. For example, using an echocardiogram, a medical professional may be able to identify: (1) the size and shape of the heart; (2) the size, thickness, and movement of the heart's walls; (3) movement of the heart; (4) the heart's pumping strength; (5) whether or not the heart valves are working properly; (6) whether or not blood is leaking backwards through the heart valves (regurgitation); (7) whether the heart valves are too narrow (stenosis); (8) whether there is a tumor or infectious grown around the heart valves; (9) problems with the outer lining of the heart (the pericardium); (10) problems with the large blood vessels that enter and leave the heart; (11) blood clots in the chambers of the heart; and (12) abnormal holes between the chambers of the heart.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions that are executed by the at least one processor to cause the at least one processor to implement an automated echocardiograph measurement extraction system. The method comprises receiving, by the automated echocardiograph measurement extraction system executing on the data processing system, medical imaging data comprising one or more medical images. The method further comprises inputting, by the automated echocardiograph measurement extraction system, the one or more medical images into a deep learning network. Moreover, the method comprises automatically processing, by the deep learning network, the one or more medical images to generate an extracted echocardiograph measurement vector output comprising one or more values for echocardiograph measurements extracted from the one or more medical images. In addition, the method comprises outputting, by the deep learning network, the extracted echocardiograph measurement vector output to a medical image viewer.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1A:
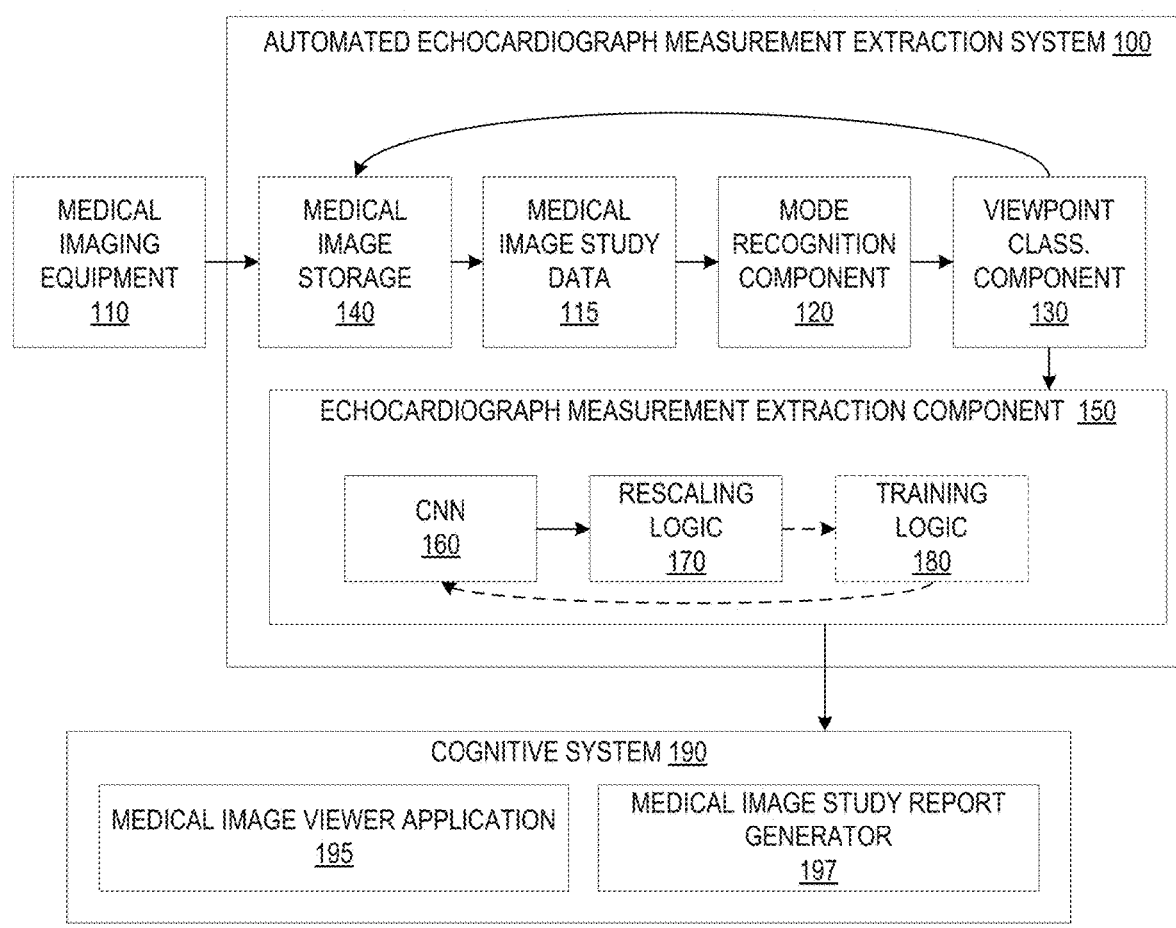
FIG. 1A is an example diagram of the primary operational components of an automated echocardiograph measurement extraction system in accordance with one illustrative embodiment.

As discussed above, echocardiography, i.e. the ultrasound study of the heart, is a common tool for measuring heart health with regard to a variety of factors. With echocardiography, different modes (e.g., A-mode, where a single transducer scans a line through the body with the echoes plotted as a function of depth, or B-mode which displays the acoustic impedance of a two-dimensional cross-section of tissue) and viewpoints of medical images are taken at various cardiac phases. In evaluating and treating patients with regard to cardiac conditions, clinicians and other medical personnel often require that measurements of the anatomical structures of the heart, e.g., the size of the chambers of the heart, the thickness of the walls of the heart, measurements regarding the aorta, pulmonary veins, valves, etc., be determined. Such measurements often are indicative of different types of cardiac medical conditions. For example measuring inter-ventricular septum and posterior wall thickness can be used to diagnose hypertrophy. As another example, left ventricle (LV) diastolic diameter, LV diastolic Diameter/BSA or LV Diastolic Diameter/height can be used to categorize a patient's case into normal, mildly abnormal, moderately abnormal or severely abnormal using clinical guidelines on the measurements. However, generating such measurements is a manual process requiring trained ultrasound sonographers to manually measure and record heart measurements of each patient and compile these measurements into a medical report document. Manual processes are time consuming, resource intensive, subject to human error, and may result in incomplete sets of measurements due to such human error.

Thus, automated mechanisms that may themselves generate a complete set of measurements of anatomical structures of the heart from echocardiograph medical images would be of great benefit in providing decision support services. Such an automated mechanism implemented in a specifically configured computing device accelerates the process of generating an echocardiography medical report document and expedites workflow. From a healthcare provider viewpoint, an automated mechanism of this sort may remove the necessity for having a human sonographer manually measure and record measurements of cardiac anatomical structures which improves the efficiency of the echocardiography workflow and pipeline, leading to better treatment of the patient as well as more reimbursements for medical personnel and value for healthcare providers.

The illustrative embodiments provide mechanisms for providing automated extraction of measurements for cardiac anatomical structures from echocardiograph images. The automated mechanism of the illustrative embodiments may perform such measurement extraction without having to perform image segmentation, i.e. without having to perform a process by which the medical image is partitioned into different meaningful segments that correspond to different tissue classes, organs, pathologies, or other biologically relevant structures. Because image segmentation may be a time-consuming process, the ability to remove the segmentation process from the evaluation of echocardiograph images accelerates the process of generating cardiac medical report documentation associated with an echocardiograph image set and expedites the overall workflow. Moreover, segmentation is not readily available in medical records and therefore, to generate a high-performance segmentation unit, a large amount of segmentations need to be produced by human experts, which is generally not feasible. However, with the illustrative embodiments, images and corresponding measurements are used for training, both of which are readily available in a patient record. Therefore, large scale training is made possible with the mechanisms of the illustrative embodiments which do not require image segmentation.

With the mechanisms of the illustrative embodiments, an automated measurement extraction engine is provided that operates on one or more images that are input to the automated measurement extraction engine and provides as output a corresponding set of measurements of anatomical structures present in the medical image(s). The automated measurement extraction engine may employ a trained machine learning or deep learning network (hereafter referred to as the "trained network"), such as a neural network, Support Vector Machine, Random Forest, or Multi-Layer Perceptrons (MLPs), which generates the measurements without performing image segmentation. The trained network estimates the measurements based on the learning of which measurements are obtained from which types of images through a training process applied to the network.

In one illustrative embodiment, multi-layer convolutional neural network (CNN) models are used to concatenate the feature vectors of medical images, e.g., echocardiograph images, using multiple views at the same time to generate measurements of anatomical structures present in the medical images. Generating an array of measurements makes the training of the CNN more accurate because correlated measurements help increase accuracy and the CNN learns the correlations between the multiple measurements. This learning indicates that there are certain views in which certain measurements are made and some of these measurements have correlations.

These measurements may be used for diagnosis using clinical knowledge, for example, in the form of guidelines and the like, which may be applied by a cognitive system. In some cases, the measurements may be used to augment the medical images that are the source of the measurements, such as by way of annotations or projections on the input medical images. This allows the human sonographer to modify the measurements when needed to correct them, with the resulting feedback being used to perform additional training of the CNN, either during the training phase of the CNN or even after deployment such that dynamic ongoing training of the CNN may be performed.

Because the trained network, or trained CNN, knows which images provide which types of measurements, in addition to, or alternative to, the diagnosis decision support mentioned above and the medical image augmentation noted above, the automated measurement extraction engine may perform additional operations for advising technicians and other medical personnel as to the types of images needed in order to complete a echocardiography medical imaging study of the patient and may also inform the technician when the echocardiography medical imaging study has been completed, i.e. all necessary measurements needed for the particular study have been obtained from the images captured. As a result, excess expenditure of human and equipment resources in obtaining unneeded medical images is minimized. Moreover, as a result, the probability of generating incomplete echocardiography medical reports in which measurements are missing is minimized.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
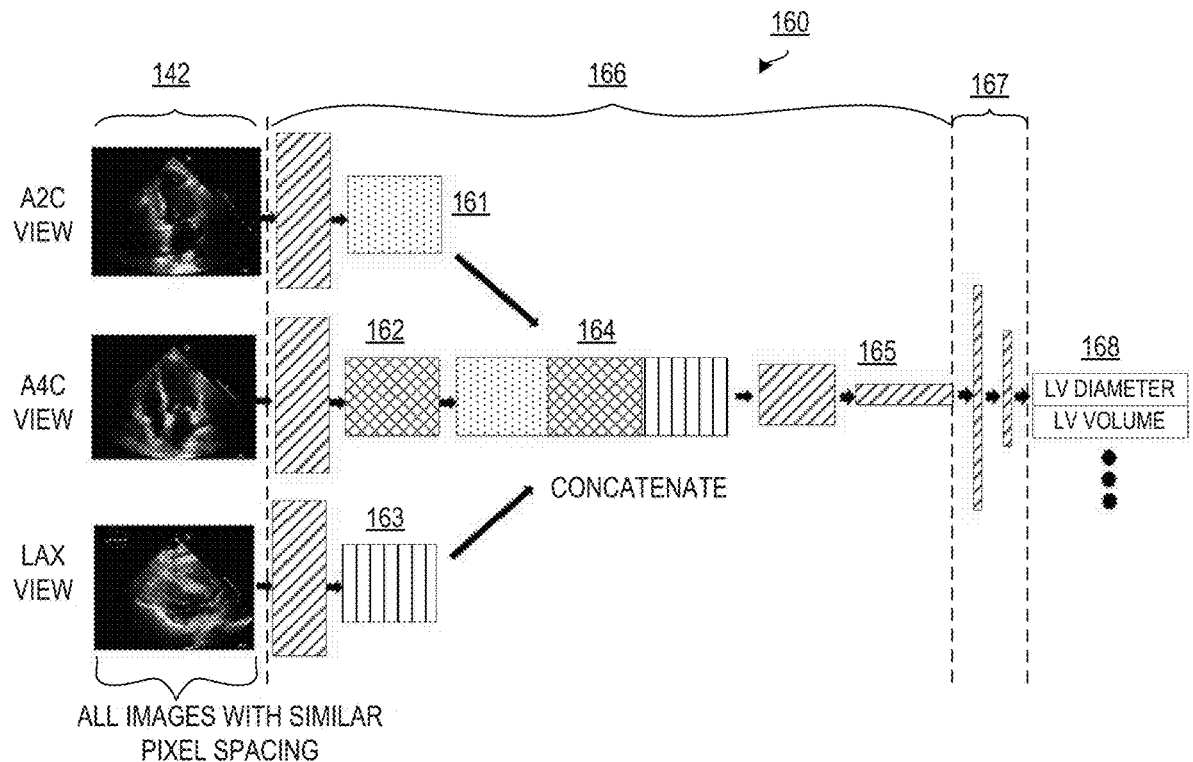
FIGS. 1B and 1C are example diagrams of embodiments of a convolutional neural network (CNN) and corresponding data flow for automatically extracting echocardiograph measurements from medical images in accordance with one illustrative embodiment.
Figure 1C:
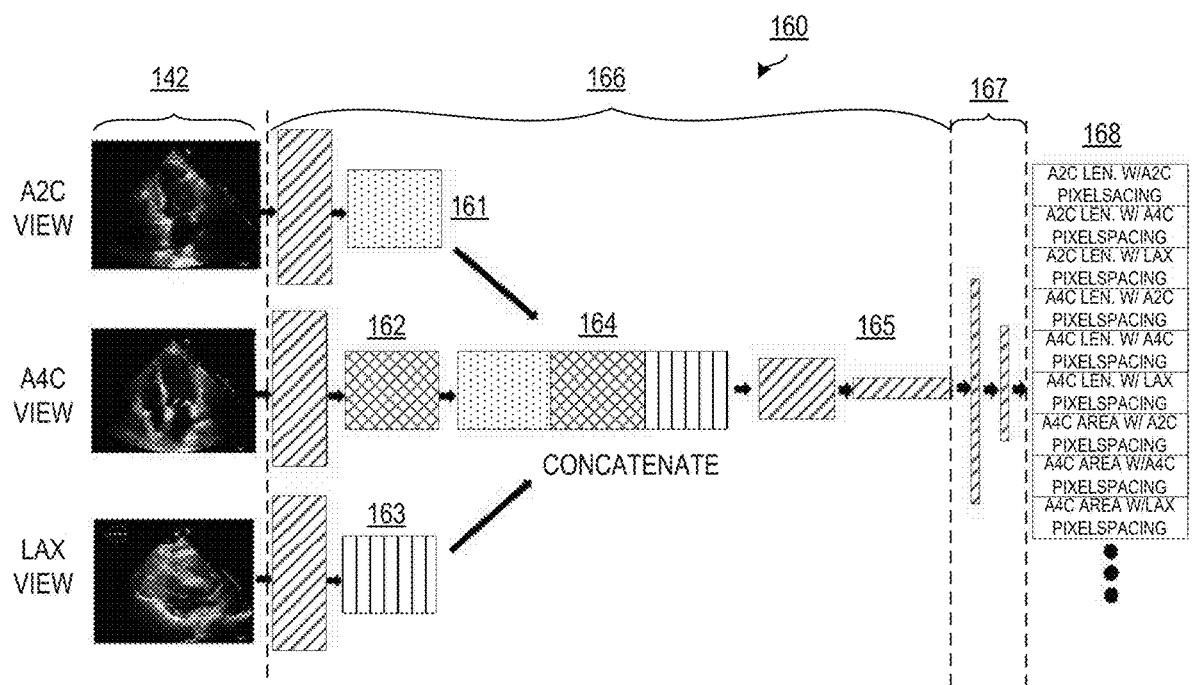

FIG. 1A illustrates an example diagram of the primary operational components of an automated echocardiograph measurement extraction system in accordance with one illustrative embodiment. FIGS. 1B and 1C are example diagrams of a detailed arrangement of layers of a CNN according to example embodiments which may be used to implement the CNN 160 in FIG. 1A, for example, and a corresponding workflow for extracting echocardiograph measurements from medical images, such as an echocardiograph images, in accordance with one illustrative embodiment. FIG. 1B is an example diagram of a data flow through a convolutional neural network (CNN) for automatically extracting echocardiograph measurements from medical images in accordance with one illustrative embodiment in which the pixels have similar pixel spacings whereas FIG. 1C is an example diagram of a data flow through a CNN for automatically extracting echocardiograph measurements from medical images in accordance with an illustrative embodiment in which each image has its own pixel spacing. The FIGS. 1A-1C will be addressed in combination in the following description of the example operation of a normality classifier in accordance with one illustrative embodiment.

As shown in FIGS. 1A-1C, in one illustrative embodiment, echocardiograph measurements are extracted from echocardiograph images having a variety of different viewpoints as obtained from echocardiograph equipment 110. It should be appreciated that various types of echocardiograph equipment 110 may be utilized and echocardiograph images may be provided in different modes, e.g., A-Mode, B-Mode, Doppler, M-Mode, etc. The echocardiograph equipment 110 captures images using an associated mode and may capture multiple images of the patient's anatomy, e.g., the chest, and in particular the heart in the case of an echocardiography image, from a variety of different viewpoints to compile a medical imaging study 115 of the patient which may be stored in the medical image storage 140 of the automated echocardiograph measurement extraction system 100. The medical imaging study 115 may be stored as one or more data structures, e.g., a separate data structure for each captured medical image, medical imaging study, or the like, in a medical image storage system 140 in association with an identifier of the patient and/or electronic medical records (EMRs) of the patient.

As shown in FIG. 1A, during a first stage of operation within the automated echocardiograph measurement extraction system 100 after receiving the medical image study data 115 from the medical imaging equipment 110, a mode recognition component 120, which may be implemented as a machine learning or deep learning system, such as a neural network or other machine learning/deep learning system, is utilized to identify for each medical image in the study data 115, a specific mode and viewpoint of the medical image. For example, a medical imaging study may have approximately 80 to 100 medical images in a single study, which are each automatically sorted into their corresponding modes and viewpoints. That is, taking echocardiography as an example, such echocardiography images may be acquired with different modes (B-Mode, Doppler, M-Mode, etc.) and at different viewpoints (parasternal long axis or 2, 3, 4, 5-chamber view, etc.). Therefore, at the first stage of operation, the mode recognition component 120 analyzes each of the medical images in the medical image study data 115 to classify the medical image into different modes. The machine/deep learning system of the mode recognition component 120 may be trained using various labeled or annotated medical images that are of different modes such that the mode recognition component is able to receive a medical image, analyze characteristics of the medical image, and classify the medical image into different modes. In one illustrative embodiment, the mode recognition component 110 may be trained and may operate using Digital Imaging and Communications in Medicine (DICOM) tag analysis and image processing for the mode classification of the incoming medical images. It should be appreciated that the mode recognition component need not be a machine/deep learning solution and instead a combination of DICOM tags and image processing can be used to classify the image modes without having to perform machine/deep learning.

A viewpoint classification component 130, which again may be implemented as a machine learning or deep learning system, may be used to classify the image into different viewpoints. The machine/deep learning viewpoint classification component 130 (or viewpoint classifier) may again be trained using medical images annotated or labeled by a specialist in a training phase with the particular viewpoint information so that the trained viewpoint classification component 130 is able to classify new medical images of various modes with regard to their viewpoint based on the similarity of the characteristics of the medical image to those upon which the training is performed.

The medical images of the medical image study data 115 that are captured by the echocardiograph equipment 110, after having been classified according to their mode and viewpoint by the mode recognition component 120 and viewpoint classification component 130, may be dynamically stored in the medical image storage system 140 as the medical imaging study of the patient is ongoing and the operations of the automated echocardiograph measurement extraction system 150 of the illustrative embodiments may be dynamically performed on sets of the captured images or in response to a request from a user, such as a sonographer or other technician or operator of the echocardiography equipment 110. Alternatively, the operations of the automated echocardiograph measurement extraction system 150 may operate on stored medical images in the medical image storage system 140 after one or more medical imaging studies are conducted on one or more patients.

In one illustrative embodiment, based on the classification of mode by the mode recognition component 120, medical images of a mode of interest may be selected from those that are stored in the medical image storage 140, for a particular patient, for use in training/testing, or runtime execution. For example, in one illustrative embodiment, B-mode echocardiography images are selected as these are currently the types of images most frequently used for measurements in modern practice, but any other modes may be used without departing from the spirit and scope of the present invention. The B-mode echocardiography images are selected and may have a variety of different viewpoints identified by the viewpoint classification component 130. While in one illustrative embodiment, the echocardiograph measurement extraction system component 150 may operate on B-mode echocardiography images, the illustrative embodiments are not limited to such and the mechanisms of the illustrative embodiments may instead be implemented with regard to any mode, or combination of modes, without departing from the spirit and scope of the illustrative embodiments. In some embodiments, separate instances of the echocardiograph measurement extraction component 150 may be implemented for different modes, e.g., one instance for B-mode medical images, one instance for M-mode medical images, and one instance for Doppler mode medical images.

The automated echocardiograph measurement extraction component 150 comprises a convolutional neural network (CNN) 160 which is trained, such as by way of training logic 180, to learn which viewpoints (or "views") are relatively better to use for particular types of measurements, where the term "measurements" as used herein is referring to measurements of physical characteristics (e.g., length, width, diameter, thickness, etc.) of physical anatomical structures from the representation of these physical anatomical structures in medical images. By training the CNN 160 as a regression model, the CNN 160 learns abstractions of the measurements. That is, a deep learning convolutional neural network learns higher abstractions of an image as it goes deeper. An example is that the first layer learns edges but higher levels learn shapes, such as circles or rectangles, and yet higher layers learn higher abstractions such as complex shapes, such as faces. With the illustrative embodiments, the CNN 160 is trained to learn the measurements as an abstraction of the input layer in the output layer. Here again, the first layer learns basic edges and such, and as the CNN 160 goes deeper, the layers learn higher level abstractions, such as measurements.

It should be appreciated that once the CNN 160 is trained, the training logic 180 of the echocardiograph measurement extraction component 150 need not be included in the echocardiograph measurement extraction component 150 which his deployed at user sites or used to process runtime requests for echocardiograph measurement extraction from medical images. This is the reason the training logic 180 is shown with dashed lines in FIG. 1A. Thus, once a training phase of development of the echocardiograph measurement extraction component 150 is complete, only the trained CNN 160 and rescaling logic 170 are utilized to process new medical images and extracted echocardiograph measurements from such medical images.

It should be noted that medical images, such as echocardiography images, have pixel spacing (the physical distance between two pixels on the image) which is absent in general images acquired by a camera, for example. Pixel spacing allows one to make physical measurements. For example, using an echocardiography image one can measure the interventricular wall thickness to be 7 mm, however, for a conventional digital camera, if one takes a picture of a wheel, one can measure the diameter of the camera in number of pixels, but will have no way of converting that to a physical measurement, e.g., cm or mm, of the wheel diameter because the distance between two pixels of a camera image are not a representative of the physical real distance between those two corresponding points.

Since the pixels in the medical images have a physical distance between them, the measurements obtained from these medical images are therefore in a physical space, e.g., in centimeters, for example. CNNs in general, and thus, the CNN 160, are blind to the pixel spacing in such medical images. Therefore, the measurements generated from the medical images obtained from the medical image storage 140, e.g., echocardiograph images, are rescaled to the pixel space, i.e. the measurements are made in numbers of image pixels and not in physical space where the measurement units are, for example, in centimeters. Since each image pixel spacing is known, a conversion from pixels to physical dimensions is made possible. In general, medical images from different views have different pixel spacing. Therefore, the same measurement may translate to a different number of pixels in pixel space for each view.

For example, consider a situation of an inter-ventricular wall thickness of 7 mm. There may be two images from different viewpoints or even two images of the same viewpoint but with different imaging depth with, for example, 1 mm and 0.5 mm pixel spacings. In this case, the IV wall appears as 7 and 14 pixels wide walls in these two images, respectively. Since it is known what the pixel spacing of the images is, it is known that a 7 pixel wide wall on an image with 1 mm pixel spacing has the same thickness as a 14 pixel wide wall on another image with 0.5 pixel spacing. However, as mentioned above, the machine learning/deep learning network is blind to the pixel spacing. When the network is trained, for example, an image is provided as an input and a measurement is generated as an output. Now in this example case, if both of these images are provided as input and the training expects 7 as an output, it will be very confusing for the network. However, if the network is given the first image as input and expects a 7 as an output, and the network is given the second image as input and expects a 14 as an output, it easier to correctly train the network.

The CNN 160, which is shown with greater detail in FIGS. 1C and 1D with regard to example embodiments, implements a multiple-view multiple-output regression model. In one illustrative embodiment, medical images 142 of the same mode, e.g., B-mode, selected from the medical image storage 140, but with different viewpoints (e.g., A2C view, A4C view, LAX view, etc.) are input at approximately the same time to the CNN 160. Measurements from echocardiography reports are concatenated into a vector as output for training. In a first illustrative embodiment, as shown in FIG. 1B, all the input images are resampled so that all have the same pixel spacing, for example, equal to the minimum of the pixel spacings. Then the physical measurements from the reports are transformed into number of pixels using this common pixel spacing. If there are multiple measurements, they are all concatenated into a measurement vector. In a second illustrative embodiment, as shown in FIG. 1C, the input images keep their original pixel spacings, however, each physical measurement from a report is transformed into a number of pixels multiple times using the pixel spacing of each image. These are concatenated into a vector. Other measurements are similarly added to these vectors.

As shown in FIG. 1B, as one example embodiment, the CNN 160 comprises multiple convolutional modules 161-165 of multiple convolutional layers 166 followed by multiple densely connected (fully connected) layers 167. Each convolutional module 161-165 contains multiple sets of convolutional layers with activation, batch normalization, and dropout layers. In the graphical depiction of FIGS. 1B and 1C, relatively smaller blocks in these figures represent that the data from a previous block is down-sampled, such as by, for example, a max pooling layer. As can be seen from the figures, the CNN 160 first analyses each of the medical image views 142 using some convolutional layers independently, e.g. convolutional layers comprising convolutional modules 161-163. Then, the CNN 160 combines the information by concatenation and processing via convolutional modules 164, and finally with fully connected layers 167.

Thus, each input image 142 having different views is followed by multiple convolutional modules 161-163, respectively, for extraction of low-level features, e.g., edges, corners, and the like, ad as the CNN 160 processes the images deeper, higher level features are extracted, such as shapes and the like. Following the extraction of the features, the outputs are concatenated together 164 and input to additional convolutional modules 165. Fully connected layers 167 take the concatenated output processed by the additional convolutional modules 165 and generates a measurement vector output 168 which comprises values for each of a plurality of measurements. In the depicted example, the measurement vector output 168 comprises measurements for left ventricle (LV) diameter, left ventricle (LV) volume, interventrical septum (IVS) width, P wave (PW) width, and the like. Thus, given multiple images with multiple different views, the CNN 160 may be trained to provide more accurate measurements. In so doing, the CNN 160 learns, by itself, to choose the best image, or a combination of images, to produce the most accurate measurements.

The training of the CNN 160 may be accomplished in a number of different ways. In one illustrative embodiment, all of a set of input training images 142 with their different viewpoints are sampled such that all of them have the same pixel spacing, as noted above and shown as an example embodiment in FIG. 1B. The resampling of an image given a same pixel spacing may be accomplished in many different ways, such as sampling every n-th pixel if such a relationship can be established between the old and new pixel spacing, or by interpolating for values between two pixels of the original image, for example. Any suitable resampling method may be used without departing from the spirit and scope of the present invention.

In some illustrative embodiments, the measurements from the reports may all be transformed into numbers of pixels by the rescaling logic 170 using the pixel spacing. As a result, the CNN 160 is trained with multiple inputs of the same pixel spacing and will produce one output for each measurement. The training of the CNN 160 may comprise an initial random or pseudo-random setting of weights of the convolutional layers. Thereafter, outputs for a given input are compared with a ground truth (measurements from reports) to identify an error in the output generated by the CNN 160. Thereafter, the weights of the convolutional layers are updated using the gradient of this error in a backpropagation manner so as to train the CNN 160.

The output for each measurement generated by the CNN 160 may be transformed into physical space using the common pixel spacing and the rescaling logic 170 and may be compared, by training logic 180, to ground truth or known measurements for the anatomical structures present in the training images, such as may be obtained from annotations, labels, or other metadata associated with the training images, e.g., measurements obtained from a text report generated by a clinician during routine clinical workflow. Such ground truth or known measurements may be manually specified by human subject matter experts (SMEs) when generating the training image dataset. In some cases, a small initial labeled or annotated set of training images may be provided and may be expanded through automated mechanisms, such as the GANs based technique described in commonly owned and co-pending U.S. patent application Ser. No. 15/850,007 entitled "Generative Adversarial Network Medical Image Generation for Training of a Classifier" and U.S. patent application Ser. No. 15/850,116 entitled "Medical Image Classification Based on a Generative Adversarial Network Trained Discriminator", or the like.

In another illustrative embodiment, such as shown in FIG. 1C, the training input images 142 are not sampled to have a common pixel spacing. Therefore, each image i from each viewpoint will have its own pixel spacing $p_i$. Instead of normalizing the input image pixel spacings, such as via the sampling of the previously described embodiment, each measurement from a report, such as an echocardiography report, produced by a clinician after evaluating an echocardiography exam, is repeatedly transformed to the pixel space using each images own pixel spacing $p_i$. That is, as a routine clinical practice, the clinicians study the exam, make measurements from the images and write them into a report that is recorded into an electronic medical record (EMR). The measurements that are used for training the CNN 160 may be extracted from these reports and transformed to the pixel space using each of the images own pixel spacing $p_i$. Therefore, if there are M viewpoints and there are N measurements in the reports, the output vector 168 will have a size of M×N. Each measurement produced by the CNN 160 and present in the output vector 168 is again transformed to the physical space using the corresponding image pixel spacing and compared to the ground truth from the report to thereby train the CNN 160 based on the identified error and backpropagation, to learn to correlate measurements and images, potentially of different viewpoints.

Once trained, the CNN 160 may be applied to new medical images, e.g., new echocardiography images such that the CNN 160 may automatically determine the optimum views from a set of selected medical images of a particular mode, but with different viewpoints, for generating particular ones of the measurements. The CNN 160 generates the output measurement vector 168 which provides estimates of the various measurements of anatomical structures present in the input set of medical images. These measurements may be in a physical space as generated by the rescaling logic 170 which is able to convert from pixel space to physical space as noted above. That is, after the CNN 160 is trained, images of different views, or viewpoints, are fed to the CNN 160 which will produce the measurement vector which contains at least one measurement transformed to a number of pixels for each of the input images. These measurements are then transformed to physical units using each image pixel spacing.

The physical measurements output by the CNN 160 may be provided by the automated echocardiograph measurement extraction system 100 to a cognitive system 190 which may itself provide a medical image viewer application 195, medical image study report generator 197, and/or other cognitive operation functionality for providing decision support services or otherwise generating output that assists medical personnel in treating patients, e.g., treatment recommendation operations, performing operations for interventional planning, such as for example performing interventional planning of transcatheter aortic valve replacement (TAVR) or other procedures for addressing cardiac conditions of a patient, or the like. For example, the cognitive system 190 may ingest clinical guidelines documentation representing the normal/abnormal range of different measurements, clinical guidelines documentation describing medical knowledge of various diseases associated with each abnormal measurement, and the like, and may evaluate the measurements generated by the CNN 160 based on the knowledge ingested from these clinical guidelines documents. "Next step" recommendations may be provided based on the evaluations that advise medical personnel on the next steps they may want to take in treating the corresponding patient. Thus, this information may be saved in a clinical knowledge database and used for "next step" recommendations, such as when the medical personnel are reviewing the patient's information, encountering the patient, or the like.

For example, the cognitive system 190 may employ a pipeline or other cognitive logic for applying rules, medical knowledge and analysis, and the like to the measurements output by the automated echocardiograph measurement extraction system 100, where these rules, medical knowledge, and the like, may be provided in electronic documents of one or more corpora that are ingested by the cognitive system 190, predefined rule sets specified by human subject matter experts, or the like. For example, a rule may state that if the LV diameter is less than a certain number of centimeters, that certain treatment recommendations should be considered for the patient. Through evidential analysis, such as based on patient electronic medical record (EMR) data and the like, other factors may be considered and scores for particular treatments may be generated so as to determine a treatment recommendation for the patient.

In some illustrative embodiments, the cognitive system 190 may perform triage support operations by classifying medical images of patients and ranking the severity of the medical conditions of the patients at least partially based on the measurements generated by the mechanisms of the illustrative embodiments. In this manner, the medical image viewer application of the cognitive system 190 may be automatically controlled by the cognitive system 190 to output the medical images of patients in accordance with the relative ranking of the medical images of that patient, based on the obtained measurements as indicated by the mechanisms of the illustrative embodiments, either alone or in addition with other cognitive evaluations of the patient's condition, e.g., evaluation of patient electronic medical record (EMR) data, other vital signs of the patient as recorded by other computing systems with which the cognitive system 190 interfaces, and the like.

Moreover, based on the identification of which medical images show abnormalities, as may be identified from the measurements generated by the mechanisms of the present invention, the corresponding most salient or relevant medical images for an individual particular patient may be output via the medical imaging viewer 195 based on the controls of the cognitive system 190. For example, there may be 80 medical images generated from an echocardiography study of the patient, each may be evaluated via the CNN 160 of the illustrative embodiments to identify corresponding measurements from the learned best viewpoint images for the particular measurements. These measurements may be compared to criteria, such as may be present in predefined rules, medical knowledge sources ingested by the cognitive system 190, medical guidelines, and the like, to identify where abnormalities may be present. The corresponding images where the measurements leading to a detection of an anomaly may be identified, i.e. the learned best images for a particular measurement, and may be presented via the medical imaging viewer 195 for viewing by medical personnel. The medical images may be displayed to the medical personnel in higher rank or order than other medical images not determined to be the best images for providing the measurements, via the medical image viewer 195.

In addition to viewing of the medical images via the medical image viewer 195 that are more representative of abnormalities in anatomical structures based on automatically extracted echocardiograph measurements, the medical image viewer application 195 may also annotate or label the medical images with the corresponding automatically extracted measurements. In this way, the measurements may be made accessible to the medical personnel when viewing the medical images. Moreover, the cognitive system 190 may also provide automated medical image study report generation via the generator 197. The medical image study report generator 197 may generate its own medical image study report or may augment an existing medical image study report by augmenting the corresponding data structure to include the automatically extracted echocardiograph measurements.

Thus, the illustrative embodiments provide a multiple input network that takes advantage of multiple different medical images of a multiple viewpoint medical imaging study associated with a patient to learn associations between types of medical image viewpoints and corresponding echocardiograph measurements. The illustrative embodiments learn which medical image viewpoints provide the most accurate estimations of echocardiograph measurements and then utilizes those to generate estimates of these measurements for future processing of medical imaging studies for patients. This process is performed without having to perform segmentation of the medical images which increases the performance of the overall system. Moreover, the mechanisms of the illustrative embodiments mitigate image quality issues of individual images and extracts information from complementary viewpoints, e.g., long-axis vs. short-axis, 2-chamber vs. 4 chamber.

The illustrative embodiments may further provide a multiple output network that takes advantage of correlation among different measurements, e.g., left ventricle diameter is correlated with left ventricle volume, which is advantageous for training. For example, there may be many measurements in echocardiography which correlate with each other, e.g., left ventricle length may be measured in 4 chamber as well as 2 chamber views. Since both measurements are measurements of the same anatomical structure, they cannot be significantly different. A similar correlation exists between the diameter and volume of the left ventricle. If one gets larger, usually, so does the other one. These correlations act as a regularizer on CNN training and improve the results. Thus, when training the CNN of the illustrative embodiments, the error evaluation of the CNN may further include evaluating such correlations between measurements to determine how to modify the operation of the CNN to reduce the loss function or error generated by the CNN, e.g., if such correlations are not maintained by the outputs generated by the CNN, then particular modifications of the weightings of convolutional layers may be adjusted accordingly to maintain such correlations.

Figure 2:
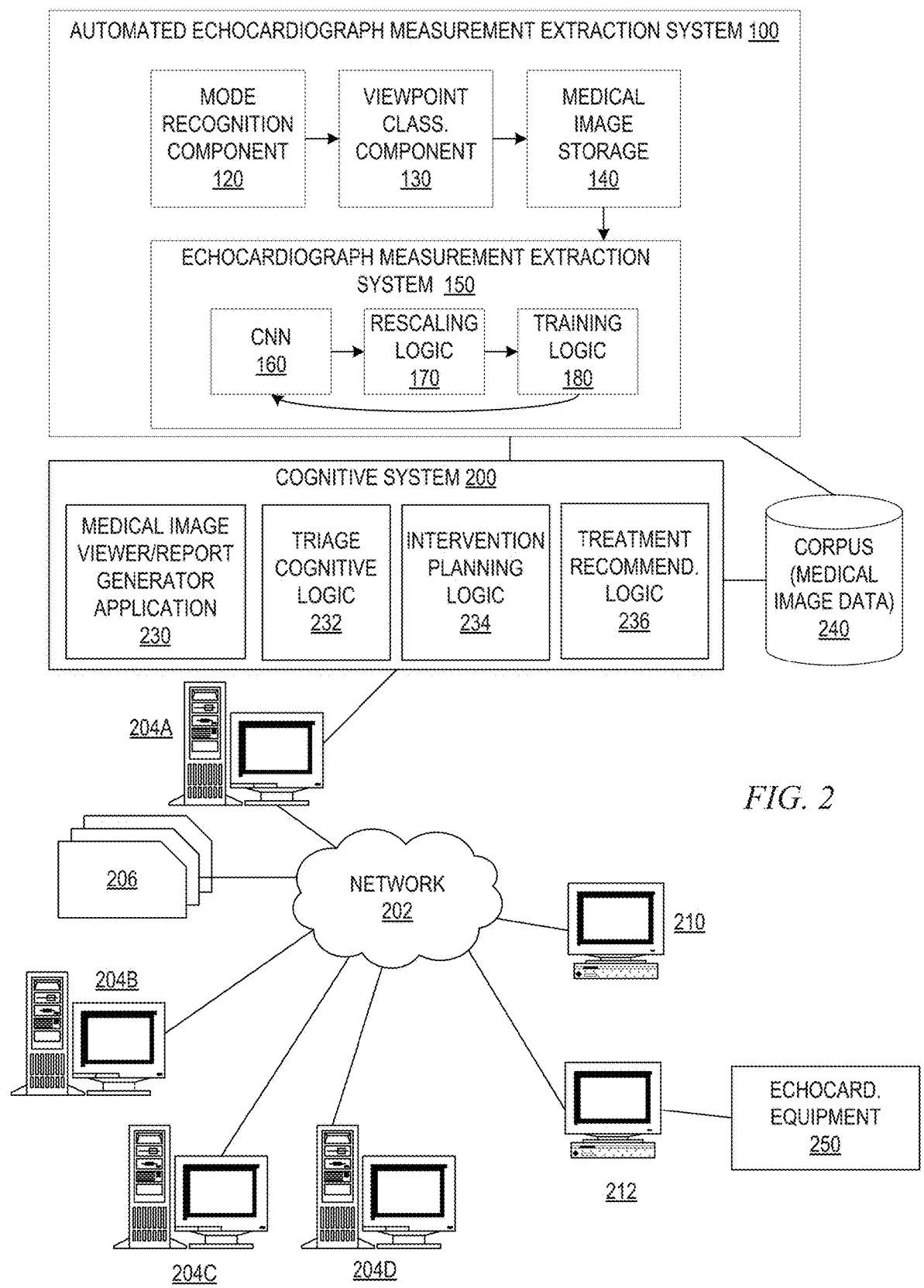
FIG. 2 depicts a schematic diagram of one illustrative embodiment of a cognitive system which operates in conjunction with an automated echocardiograph measurement extraction system in accordance with one illustrative embodiment.
Figure 3:
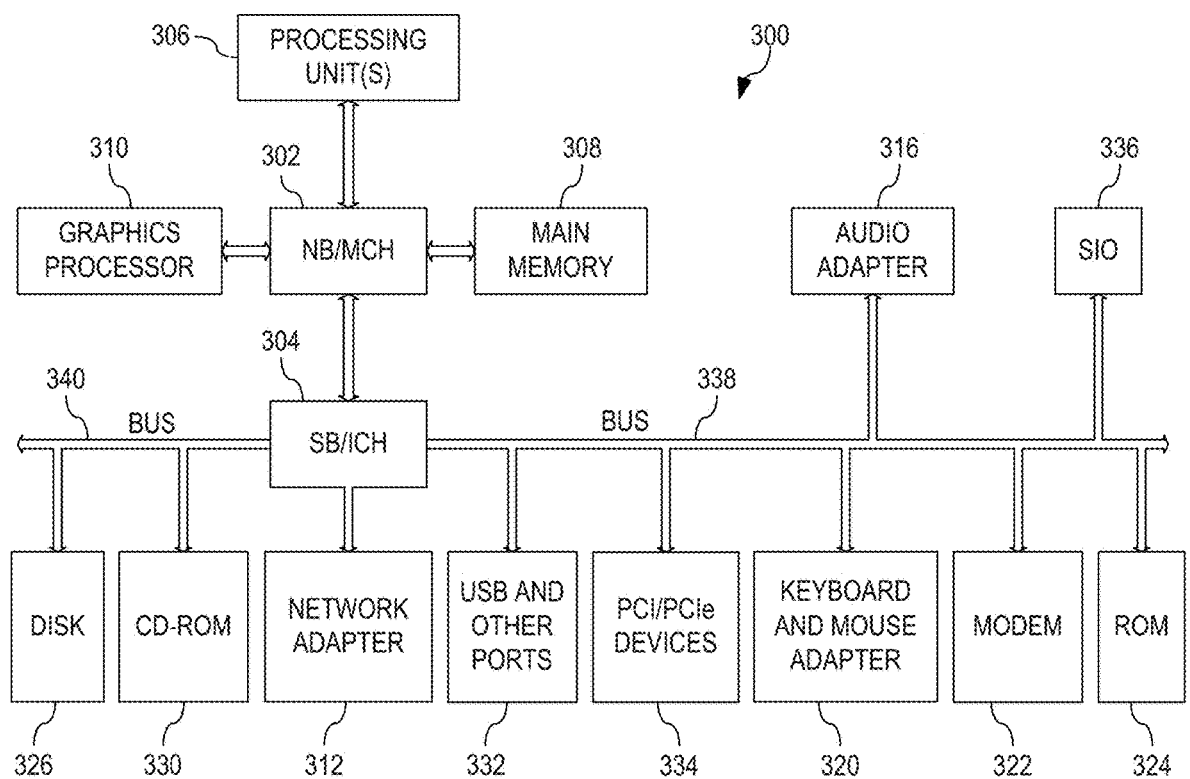
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

FIGS. 2-3 are directed to describing an example cognitive system for healthcare applications which implements a medical image viewer application 230 for viewing medical images and obtaining information about the medical images of particular patients. The cognitive system may also provide other cognitive functionality including treatment recommendations, patient electronic medical record (EMR) analysis and correlation with medical imaging data, intervention planning and scheduling operations, patient triage operations, and various other types of decision support functionality involving cognitive analysis and application of computer based artificial intelligence or cognitive logic to large volumes of data regarding patients, at least a portion of which involves the normality scoring mechanisms of the normality classifier. In some illustrative embodiments, the cognitive system may implement a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, medical image analysis logic, and the like, for example, as well as machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, medical image analysis logic, and other types of logic that emulate human thought processes using specially configured computing mechanisms. IBM Watson™ is an example of one such cognitive system with which the mechanisms of the illustrative embodiments may be utilized or in which the mechanisms of the illustrative embodiments may be implemented.

FIG. 2 depicts a schematic diagram of one illustrative embodiment of a cognitive system 200 implementing a medical image viewer/report generator application 230 in a computer network 202, and which operates in conjunction with a normality classifier, such as normality classifier 100 in FIG. 1A, in accordance with one illustrative embodiment. The cognitive system 200 may further comprise various other types of cognitive operation logic for performing cognitive operations based on analysis of received medical image data and the automatic extraction of echocardiograph measurements from medical images of medical imaging studies having various viewpoints, in accordance with the operation of the automated echocardiograph measurement extraction system 100 as previously described above. For example, the cognitive system 200 may comprise triage cognitive logic 232, intervention planning logic 234, treatment recommendation logic 236, or other cognitive operation logic as will become apparent to those of ordinary skill in the art in view of the present description.

The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like.

In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, such as medical imaging data, or the like. Other embodiments of the cognitive system 200 may be used with components, systems, sub-systems, and/or devices other than those that are depicted herein.

In some illustrative embodiments, the client computing devices 210 and 212 may be used as a mechanism for logging onto or otherwise accessing the cognitive system 200 for purposes of viewing medical imaging studies for patients and performing other cognitive operations for assisting with decision making and/or treatment of a patient by a medical professional. For example, a sonographer or other medical imaging subject matter expert (SME) may utilize a client computing device 210 to access the services and functionality provided by the cognitive system 200 and the medical image viewer/report generator application 230 to view medical images of one or more medical imaging studies stored in the corpus 240 for one or more patients and/or corresponding reports detailing the echocardiograph measurements automatically extracted from the medical images by the automated echocardiograph measurement extraction system 100. The user of the client computing device 210 may view the medical images and perform operations for annotating the medical images, adding notes to patient electronic medical records (EMRs), and any of a plethora of other operations that may be performed through human-computer interaction based on the human's viewing of the medical images via the cognitive system 200.

As noted above, in some illustrative embodiments, the cognitive system 200 may be configured to implement a request processing pipeline that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D include devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

The request processing pipeline of the cognitive system 200 may comprises a plurality of stages for processing an input question/request based on information obtained from the corpus or corpora of data 206 and/or 240. The pipeline generates answers/responses for the input question or request based on the processing of the input question/request and the corpus or corpora of data 206, 240. In some illustrative embodiments, the cognitive system 200 may be the IBM Watson™ cognitive system available from International Business Machines Corporation of Armonk, N.Y., which is augmented with the mechanisms of the illustrative embodiments described herein. More information about the pipeline of the IBM Watson™ cognitive system may be obtained, for example, from the IBM Corporation website, IBM Redbooks, as well as in Yuan et al., "Watson and Healthcare," IBM developerWorks, 2011 and "The Era of Cognitive Systems: An Inside Look at IBM Watson and How it Works" by Rob High, IBM Redbooks, 2012.

One or more of the servers 204A-C and/or client computing devices 210-212 may be associated with medical imaging equipment 250, such as echocardiography equipment, which is used to capture medical image data for a patient, such as is generally known in the art. The medical images captured may be provided to a storage system such as part of a corpus or corpora of electronic data, such as corpora 206 and/or 240. The medical image data may have associated metadata generated by the equipment and/or computing systems associated with the equipment, to provide further identifiers of characteristics of the medical image, e.g., DICOM tags, metadata specifying mode, viewpoint, or the like.

In some illustrative embodiments, the user may be an operator of echocardiography equipment 250 which is coupled to a computing device, such as client device 212 in the depicted example, which provides medical images as part of a medical imaging study to a storage, such as corpus 240, via the network 202 and corresponding server 204A. The cognitive system 200 may evaluate the medical imaging study that is being performed, identify which measurements are to be extracted from the medical images based on the type of medical imaging study, and, through the learning performed by the CNN 160 with regard to associations of medical image viewpoints and corresponding echocardiograph measurements, may determine which medical images need to be captured as part of the medical imaging study. The capture of these medical images and the extraction of the corresponding measurements extracted from the medical imaging study, may be monitored as the medical imaging study is being performed by the echocardiography equipment 250. The cognitive system 200 may determine which measurements have and have not been able to be extracted by the automated echocardiograph measurement extraction system 100 based on the learned associations of medical image viewpoints and corresponding echocardiograph measurements. Moreover, the cognitive system 200 may determine which medical images, e.g., which viewpoints, still need to be captured in order to provide the missing measurements. In addition, once all measurements have been able to be extracted by the automated echocardiograph measurement extraction system 100, the cognitive system 200 may further determine that further medical image capture is unnecessary.

The cognitive system 200 may provide indications of these various determinations to the human sonographer via the computing device 212. Thus, as the sonographer is conducting the medical imaging study of the patient, feedback is provided to the sonographer as to which medical image viewpoints still need to be captured, which measurements have been able to be extracted, and when the medical imaging study has been completed.

As shown in FIG. 2, the cognitive system 200 may operate in conjunction with the automated echocardiograph measurement extraction system 100, which comprises components 120-180 which operate in the manner previously described above with regard to FIGS. 1A-1B. The various components 120-180 implementing machine learning and/or deep learning mechanisms, such as neural networks, Support Vector Machines, Random Forest systems, Multi-Layer Perceptrons (MLPs), or the like, may be trained using atlases paired with raw images in a training medical image dataset as may be provided in corpus 240, for example. These atlases may comprise labeled or annotated medical images as may have been labeled or annotated by human subject matter experts, where these labels or annotations may comprise echocardiograph measurements associated with anatomical structures present within these medical images. In some embodiments, these training medical image datasets may be expanded using automated mechanisms, such as the GANs based automated mechanisms of the co-pending and commonly assigned U.S. Patent Applications previously referenced above.

As described previously with regard to FIGS. 1A and 1B, the automated echocardiograph measurement extraction system 100 may output echocardiograph measurements representing the physical measurements of physical characteristics of anatomical structures, such as dimensions of the ventricles, dimensions of the aorta, dimensions of veins, and other structures of the human heart. These measurements are provided to the cognitive system 200 which may implement the various cognitive system logic 230-236 to view medical images and corresponding annotations or labels generated based on the extracted measurements, generate corresponding medical imaging reports specifying the extracted measurements, perform triage operations based on the measurements, perform intervention planning, and/or generate treatment recommendations. The medical image viewer application 230 and/or other cognitive operation functionality logic 232-236 may implement one or more cognitive system request processing pipelines for performing their respective operations. In some cases, each element 230-236 may be a separate request processing pipeline which operates in parallel or sequentially with the other processing pipelines to perform the respective cognitive operations.

The medical image viewer application 230 provides the logic for rendering medical images such that a user may view the medical images and the corresponding annotations or labels based on the automatically extracted echocardiograph measurements, manipulate the view via a graphical user interface, and the like. The medical image viewer application 230 may comprise various types of graphical user interface elements for presenting medical image information to the user, some of which may include the echocardiograph measurements automatically extracted from the medical images of a medical imaging study by the automated echocardiograph measurement extraction system 100. Based on the identification of which medical images show abnormalities that influence or are represented by echocardiograph measurements extracted by the mechanisms of the present invention, the corresponding most salient or relevant medical images for an individual particular patient may be output via the medical imaging viewer application 230, as noted above.

In some illustrative embodiments, the medical image viewer application 230 may augment the rendering of a medical image with additional emphasis and/or annotation features to identify portions of the medical image where medical personnel may wish to direct their attention, e.g., highlighting regions of abnormalities or the like. That is, in addition to normal/abnormal classification and viewing of the medical images via the medical image viewer application 230 that are more representative of abnormalities in anatomical structures, shape feature deviations (compared to shape feature of normal shapes) may be turned into intensity representations in the medical images that are rendered by the medical imaging viewer application of the cognitive system 200.

Those portions of the medical images that have higher deviations from normal shapes as identified by echocardiograph measurements extracted from the medical images using the mechanisms of the illustrative embodiments, may be rendered in different colors, shades, with conspicuous annotations or labels, or the like, via the medical image viewer application based on the information provided by the mechanisms of the illustrative embodiments, such that the medical personnel are clearly shown the location of abnormality within the medical image. Various levels of abnormality, as determined from automatically extracted echocardiograph measurements by the illustrative embodiments, may be represented in the type of accentuation of the portions of the medical image utilized to direct the medical personnel's attention to that portion of the medical image, e.g., different colors, highlighting, size of text or numerical values in annotations or labels, flashing or other visual accentuation techniques, graphical elements added to the medical image, such as symbols or pictures, or the like.

In some illustrative embodiments, the cognitive system 200 may comprise triage cognitive logic 232 that performs triage support operations by classifying medical images of patients and ranking the severity of the medical conditions of the patients at least partially based on the automatically extracted echocardiograph measurements extracted by the automated echocardiograph measurement extraction system 100. In this manner, the medical image viewer application 230 may be automatically controlled by the triage cognitive logic 232 of the cognitive system 200 to output the medical images of patients in accordance with the relative ranking of the normality of the medical images of that patient as indicated by the automatically extracted echocardiograph measurements extracted by the illustrative embodiments, either alone or in addition with other cognitive evaluations of the patient's condition, e.g., evaluation of patient electronic medical record (EMR) data, other vital signs of the patient as recorded by other computing systems 204A-C or client devices 210-212, with which the cognitive system 200 interfaces, and the like.

In some illustrative embodiments, treatment recommendation logic 236 may be implemented by the cognitive system 200 which may utilize the automatically extracted echocardiograph measurements extracted by the automated echocardiograph measurement extraction system 100, along with other cognitive processing of patient information, such as may be provided in one or more patient electronic medical records (EMRs) as may be provided by corpus/corpora 206 and/or 240, to determine a treatment to be recommended to medical personnel for treating the patient. The treatment recommendation logic 236 may apply medical knowledge encoded in various sources of medical information in electronic form in the corpus or corpora 206 and/or 240 to the patient information and/or automatically extracted echocardiograph measurements extracted by the automated echocardiograph measurement extraction system 100 to determine the applicability of various candidate treatments. The candidate treatments may be evaluated based on evidential data to generate confidence scores for the various candidate treatments, and a final recommended treatment may be generated based on a ranking of the candidate treatments based on the confidence scores. In some embodiments, the automatically extracted echocardiograph measurements extracted by the automated echocardiograph measurement extraction system 100 may be used as part of the calculation of confidence scores for the various candidate treatments, e.g., as an additional scoring variable, as a weighting factor, or the like.

In some illustrative embodiments, the automatically extracted echocardiograph measurements extracted by the automated echocardiograph measurement extraction system 100 may be used by intervention planning logic 234 of the cognitive system 200 to perform intervention planning operations for planning procedures and services to treat patients based on a relative ranking of severity of patient medical conditions. For example, the automatically extracted echocardiograph measurements may be used by the cognitive system 200 to relatively rank patients, such as discussed above with the triage cognitive logic 232. The intervention planning logic 234 may identify relative severity of patient medical conditions and perform operations interactive with other facility systems, such as scheduling systems for scheduling medical personnel to treat the patient, scheduling access to facilities for performing needed procedures, scheduling medical personnel for performing medical procedures, schedule medical equipment that is to be used to perform such medical procedures, and the like. This may be done automatically and/or semi-automatically with the assistance of other human users that are involved in scheduling or otherwise performing intervention planning operations. For example, the intervention planning logic 234, potentially interacting with triage cognitive logic 232 and treatment recommendation logic 236, may send requests to personnel for specific medical procedures to be scheduled, or may go further and determine what facilities, equipment, and personnel are needed to perform a medical procedure and send specific requests for these particular facilities, equipment, and personnel, with the subsequent scheduling being done manually by the human personnel.

It should be appreciated that these are only examples of cognitive operations that may be performed based on a automatically extracted echocardiograph measurements extracted by the automated echocardiograph measurement extraction system 100. Other types of cognitive operations that may be performed in addition to, or in replacement of, those shown in FIG. 2 may be used without departing from the spirit and scope of the present invention.

As noted above, the mechanisms of the illustrative embodiments are rotted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspect of the illustrative embodiments are implemented. Data processing system 300 is an example of a computer, such as a server 204A-D or client 210-212 in FIG. 2, in which computer usable code or instructions implementing the processes for illustrative embodiments of the present invention are located. In one illustrative embodiment, FIG. 3 represents a server computing device, such as a server 204A, which, which implements a cognitive system 200 and medical image viewer application 230, where the server 204A further is specifically configured and executes hardware and/or software logic to implement the normality classifier 100 of FIGS. 1A and 2.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System P® computer system, running the Advanced Interactive Executive (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
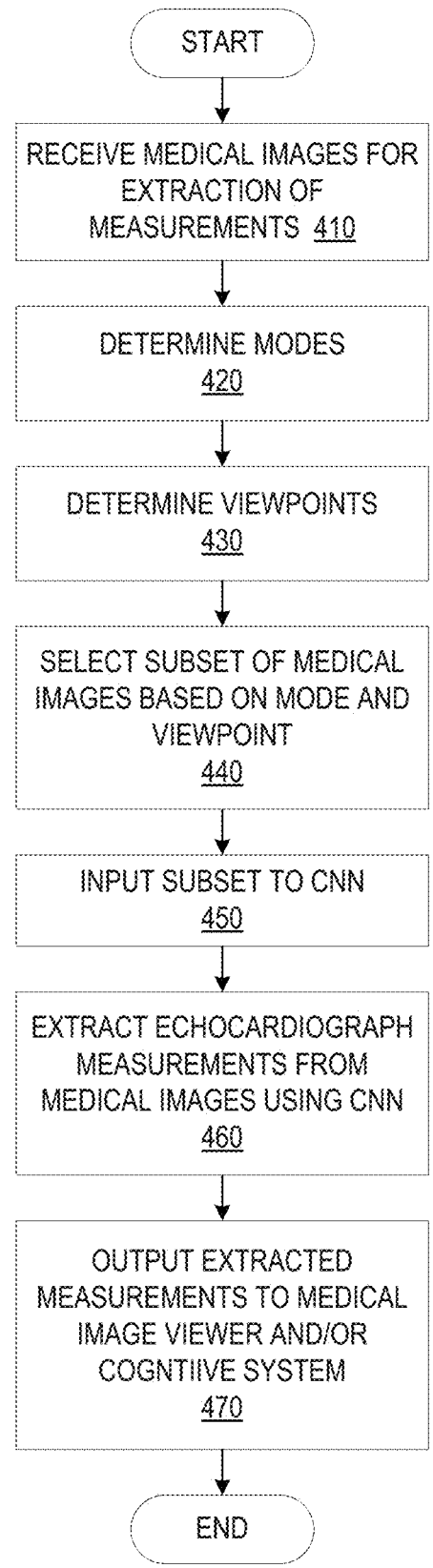
FIG. 4 is a flowchart outlining an example operation for performing normality classification of medical images in accordance with one illustrative embodiment.

FIG. 4 is a flowchart outlining an example operation for performing normality classification of medical images in accordance with one illustrative embodiment. The operation outlined in FIG. 4 may be implemented by an automated echocardiograph measurement extraction system, such as echocardiograph measurement extraction system 100 described above with regard to FIGS. 1A-2. The operation outlined in FIG. 4 is for purposes of extracting echocardiograph measurements from medical images of a medical imaging study having various different viewpoints. The operation assumes that the various machine learning and/or deep learning mechanisms have already been trained in the manner previously described above. Moreover, while not shown in FIG. 4, the extracted echocardiograph measurements may be used as a basis for performing medical image rendering by a medical image viewer application, medical imaging study report generation, and/or may be used as a basis for performing various cognitive operations.

As shown in FIG. 4, the operation starts by receiving a plurality of medical images as part of a medical imaging study for extraction of echocardiograph measurements (step 410). The modes of the received medical images are determined (step 420) and the viewpoints of the medical images are classified (step 430). A subset of medical images is selected based on a selected mode and viewpoints, where the subset of medical images may have various different viewpoints (step 440). The selected medical images of the same mode, but with varying viewpoints, are input to a trained convolutional neural network (step 450) which operates on the medical image data to extract echocardiograph measurements from the medical images based on a learned association of medical image viewpoints and corresponding echocardiograph measurements (step 460). The extracted echocardiograph measurements are then output to a cognitive system and/or medical image viewer for reporting of the extracted echocardiograph measurements and/or performance of one or more cognitive operations (step 470). The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to implement an automated echocardiograph measurement extraction system, the method comprising:

receiving, by the automated echocardiograph measurement extraction system executing on the data processing system, medical imaging data comprising one or more medical images;

inputting, by the automated echocardiograph measurement extraction system, the one or more medical images into a deep teaming network;

automatically processing, by the deep learning network, the one or more medical images to generate an extracted echocardiograph measurement vector output comprising one or more values for echocardiograph measurements extracted from the one or more medical images; and outputting, by the deep learning network, the extracted echocardiograph measurement vector output to a medical image viewer, wherein outputting, by the deep learning network, the extracted echocardiograph measurement vector output to a medical image viewer further comprises:
identifying, by the automated echocardiograph measurement extraction system, for each type of echocardiograph measurement required to be extracted from the one or more medical images, a corresponding medical image viewpoint that provides an optimum viewpoint for generating the type of echocardiograph measurement; and
determining, by the automated echocardiograph measurement extraction system, for each type of echocardiograph measurement, whether the one or more medical images comprises at least one medical image having a viewpoint corresponding to the optimum viewpoint.

2. The method of claim 1, wherein the one or more medical images comprise a one or more B-mode echocardiography images of a patient.

3. The method of claim 1, wherein automatically processing the one or more medical images to generate an extracted echocardiograph measurement vector output is performed without performing image segmentation on the one or more medical images.

4. The method of claim 1, wherein the deep learning network comprises a multi-layer convolutional neural network.

5. The method of claim 1, wherein the one or more medical images comprise a plurality of medical images wherein at least two medical images in the plurality of medical images have different viewpoints, and wherein automatically processing the one or more medical images to generate an extracted echocardiograph measurement vector output comprises concatenating feature vectors of the plurality of medical images.

6. The method of claim 1, wherein outputting, by the deep learning network, the extracted echocardiograph measurement vector output to a medical image viewer further comprises:
annotating, by the automated echocardiograph measurement extraction system, the one or more medical images to include the one or more values for echocardiograph measurements; and
displaying the annotated one or medical images via the medical image viewer.

7. The method of claim 1, wherein outputting, by the deep learning network, the extracted echocardiograph measurement vector output to a medical image viewer further comprises, for each type of echocardiograph measurement:
in response to the one or more medical images not comprising at least one medical image having a viewpoint corresponding to the optimum viewpoint, outputting a notification to a user that at least one additional medical image is to be captured of the patient, and specifying the optimum viewpoint for the corresponding type of echocardiograph measurement.

8. The method of claim 1, wherein outputting, by the deep learning network, the extracted echocardiograph measurement vector output to a medical image viewer further comprises:
determining, by the automated echocardiograph measurement extraction system, whether each type of echocardiograph measurement required to be extracted from the one or more medical images has been extracted from the one or more medical images; and
outputting, by the automated echocardiograph measurement extraction system, a notification to a user that capturing of medical images has been completed.

9. The method of claim 1, further comprising:
training the deep learning network, based on an annotated training image data set, to extract echocardiograph measurements from medical images.

10. A computer program product comprising a computer readable storage medium having a computer readable program stored therein, wherein the computer readable program, when executed on a data processing system, causes the data processing system to implement an automated echocardiograph measurement extraction system that operates to:
receive medical imaging data comprising one or more medical images;
input the one or more medical images into a deep learning network;
automatically process, by the deep learning network, the one or more medical images to generate an extracted echocardiograph measurement vector output comprising one or more values for echocardiograph measurements extracted from the one or more medical images; and
output, by the deep learning network, the extracted echocardiograph measurement vector output to a medical image viewer, wherein the computer readable program further causes the automated echocardiogram measurement extraction system to output, by the deep learning network, the extracted echocardiograph measurement vector output to a medical image viewer further at least by:
identifying, by the automated echocardiograph measurement extraction system, for each type of echocardiograph measurement required to be extracted from the one or more medical images, a corresponding medical image viewpoint that provides an optimum viewpoint for generating the type of echocardiograph measurement; and
determining, by the automated echocardiograph measurement extraction system, for each type of echocardiograph measurement, whether the one or more medical images comprises at least one medical image having a viewpoint corresponding to the optimum viewpoint.

11. The computer program product of claim 10, wherein the one or more medical images comprise a one or more B-mode echocardiography images of a patient.

12. The computer program product of claim 10, wherein the computer readable program further causes the automated echocardiograph measurement extraction system to automatically process the one or more medical images to generate an extracted echocardiograph measurement vector output without performing image segmentation on the one or more medical images.

13. The computer program product of claim 10, wherein the deep learning network comprises at least one of a multi-layer convolutional neural network.

14. The computer pr product of claim 10, wherein the one or more medical images comprise a plurality of medical images wherein at least two medical images in the plurality of medical images have different viewpoints, and wherein the computer readable program further causes the automated echocardiograph measurement extraction system to automatically process the one or more medical images to generate an extracted echocardiograph measurement vector output at least by concatenating feature vectors of the plurality of medical images.

15. The computer program product of claim 10, wherein the computer readable program further causes the automated echocardiograph measurement extraction system to output, by the deep learning network, the extracted echocardiograph measurement, vector output to a medical image viewer further at least by:
   annotating, by the automated echocardiograph measurement extraction system, the one or more medical images to include the one or more values for echocardiograph measurements; and
   displaying the annotated one car medical images via the medical image viewer.

16. The computer program product of claim 10, wherein the computer readable program further causes the automated echocardiograph measurement extraction system to output, by the deep learning network, the extracted echocardiograph measurement vector output to a medical image viewer at least by, for each type of echocardiograph measurement:
   in response to the one or more medical images not comprising at least one medical image having a viewpoint corresponding to the optimum viewpoint, outputting a notification to a user that at least one additional medical image is to be captured of the patient, and specifying the optimum viewpoint for the corresponding type of echocardiograph measurement.

17. The computer program product of claim 10, wherein the computer readable program further causes the automated echocardiograph measurement extraction system to output, by the deep learning network, the extracted echocardiograph measurement vector output to a medical image viewer at least by:
   determining, by the automated echocardiograph measurement extraction system, whether each type of echocardiograph measurement required to be extracted from the one or mere medical images has been extracted from the one or more medical images; and
   outputting, by the automated echocardiograph measurement extraction system, a notification to a user that capturing of medical images has been completed.

18. An apparatus comprising:
   a processor; and
   a memory coupled to the processor, wherein the memory comprises instructions which, when executed by the processor, cause the processor to implement an automated echocardiograph measurement extraction system that operates to:
   receive medical imaging data comprising one or more medical images;
   input the one or more medical images into a deep learning network;
   automatically process, by the deep learning network, the one or more medical images to generate an extracted echocardiograph measurement vector output comprising one or more values for echocardiograph measurements extracted from the one or more medical images; and
   output, by the deep learning network, the extracted echocardiograph measurement vector output to a medical image viewer, wherein the instructions further cause the automated echocardiograph measurement extractions system to output, by the deep learning network, the extracted echocardiograph measurement vector output to a medical image viewer further at least by:
   identifying, by the automated echocardiograph measurement extraction system, for each type of echocardiograph measurement required to be extracted from the one or more medical images, a corresponding medical image viewpoint that provides an optimum viewpoint for generating the type of echocardiograph measurement; and
   determining, by the automated echocardiograph measurement extraction system for each type of echocardiograph measurement, whether the one or more medical images comprises at least one medical image having a viewpoint corresponding to the optimum viewpoint.

* * * * *